(12) United States Patent
Handa et al.

(10) Patent No.: US 9,433,802 B2
(45) Date of Patent: Sep. 6, 2016

(54) RADIOTHERAPY APPARATUS CONTROL APPARATUS AND SPECIFIC SITE POSITION MEASURING METHOD

(75) Inventors: Takanobu Handa, Hiroshima (JP); Shuji Kaneko, Hiroshima (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 949 days.

(21) Appl. No.: 12/999,782

(22) PCT Filed: Mar. 10, 2009

(86) PCT No.: PCT/JP2009/054587
§ 371 (c)(1),
(2), (4) Date: Dec. 17, 2010

(87) PCT Pub. No.: WO2010/103623
PCT Pub. Date: Sep. 16, 2010

(65) Prior Publication Data
US 2011/0087061 A1   Apr. 14, 2011

(51) Int. Cl.
*A61N 5/00* (2006.01)
*A61N 5/10* (2006.01)

(52) U.S. Cl.
CPC ..... *A61N 5/1049* (2013.01); *A61N 2005/1061* (2013.01); *A61N 2005/1062* (2013.01)

(58) Field of Classification Search
CPC .................. A61N 2005/1062; A61N 5/1065; A61N 5/1069
USPC .......................................................... 600/1
See application file for complete search history.

(56) References Cited

U.S. PATENT DOCUMENTS

| 5,727,554 A | 3/1998 | Kalend et al. |
| 2005/0054916 A1 | 3/2005 | Mostafavi |
| 2007/0297566 A1 | 12/2007 | Urano et al. |

FOREIGN PATENT DOCUMENTS

| JP | 2001-505082 A | 4/2001 |
| JP | 2004-166975 A | 6/2004 |
| JP | 2005-236508 A | 9/2005 |
| JP | 3785136 B2 | 6/2006 |
| JP | 2007-503926 A | 3/2007 |
| JP | 2007-156771 A | 6/2007 |
| JP | 2008-456 A | 1/2008 |
| JP | 4126318 B2 | 7/2008 |

OTHER PUBLICATIONS

Notice of Allowance for corresponding Japanese Application No. 2011-503596 mailed Oct. 5, 2012 with English translation.
Chinese Decision to Grant a Patent, issued Nov. 14, 2014, for Chinese Application No. 200980122626.7, along with an English translation.

*Primary Examiner* — Catherine B Kuhlman
*Assistant Examiner* — Shannon McBride
(74) *Attorney, Agent, or Firm* — Birch, Stewart, Kolasch & Birch, LLP

(57) ABSTRACT

A specific site location measuring includes: calculating matching degrees based on a plurality of transmission images imaged by use of radiation transmitting through a specimen and a template set; selecting a template transmission image from the plurality of transmission images based on the matching degrees; adding a new template generated based on the template transmission image, to the template set; imaging a location measurement transmission image by use of radiation transmitting through the specimen; selecting an optimal template that is the most similar to a portion of the location measurement transmission image, from the template set by performing pattern matching of each of templates of the template set with the location measurement transmission image; and calculating a specific site location based on the location measurement transmission image and the optimal template.

8 Claims, 10 Drawing Sheets

RADIOTHERAPY APPARATUS CONTROL APPARATUS AND SPECIFIC SITE POSITION MEASURING METHOD

TECHNICAL FIELD

The present invention relates to a radiotherapy apparatus control apparatus and a specific site location measuring method, and more particularly relates to a radiotherapy apparatus control apparatus and a specific site location measuring method, which are used when therapeutic radiation is irradiated to an affected site (tumor) inside a human body.

BACKGROUND ART

Radiotherapy is known which treats a patient by irradiating therapeutic radiation to an affected site (tumor). The radiotherapy apparatus includes an imager system for imaging a transmission image of the patient, a therapeutic radiation irradiating unit for irradiating therapeutic radiation; and a driving unit for driving the therapeutic radiation irradiating unit. The radiotherapy apparatus calculates a location of the affected site in accordance with the transmission images, and drives the therapeutic radiation irradiating unit by controlling a driving unit to irradiate the therapeutic radiation to the location. In such a radiotherapy apparatus, the exposure dose of the therapeutic radiation irradiated to normal cells can be decreased, as compared with the dose of the therapeutic radiation irradiated to the cells of the affected site. In the foregoing radiotherapy, the affected site of the patient is desired to be measured with higher precision.

Japanese Patent Publication (JP 2007-156771A) discloses an image detecting and tracking apparatus that can accurately detect a target from an input image and continuously track it. The image detecting and tracking apparatus includes an image input unit for inputting a video image to acquire an image for each frame; a moving region calculating section that detects a movement region of the images acquired by the image input unit and outputs a detection result as numerical data for each predetermined region of each frame; a pattern detecting and calculating section that detects a pattern of a detection target in the images acquired by the image input unit and outputs the detection result as numerical data for each predetermined region of each frame; a pattern tracking and calculating section that tracks the pattern of the detection target detected by the pattern detecting and calculating section from the image for each frame acquired by the image input unit and outputs the tracking result as numerical data; an existence degree synthesizing section that synthesizes the respective numerical data outputted by the moving region calculating section, the pattern detecting and calculating section and the pattern tracking and calculating section; and a pattern window controller that sequentially calculates an in-frame location of the pattern of the detection target as a pattern window for each frame on the basis of the numerical data synthesized by the existence degree synthesizing section.

Japanese Patent Publication (JP 2005-236508A) discloses an automatic tracking apparatus that can carry out stable tracking without any stop of the tracking when a target such as an invader in an image is tracked. The automatic tracking apparatus inputs images picked up by an imaging unit and tracks the target in the images. The automatic tracking apparatus includes a template matching unit for carrying out a correlation operation between a template image indicating a feature of the target and the inputted image; a shape change detecting section for detecting the shape change of the target; and a template holding control unit for controlling an update algorism of the template image on the basis of the processed result by the shape change detecting section.

Japanese Patent No. 4,126,318 discloses a radiotherapy apparatus control apparatus for detecting a predetermined target site of a specimen with higher precision. The radiotherapy apparatus control apparatus is for controlling a radiotherapy apparatus, which includes a therapeutic radiation irradiating unit for irradiating a therapeutic radiation; an imager for generating images of the specimen from the radiation transmitted through the specimen; a feature site extracting section that generates a plurality of projection templates each indicating changes in projection brightness when a plurality of image templates having different location relation of a target site of the specimen and a non-target site of the specimen are projected in one direction, and generates a feature site template indicating a portion common to the plurality of projection templates; and an affected site location calculating section that performs pattern matching of the feature site template with the changes in the projection brightness when the images are projected in one direction to calculate the location of the target site.

Japanese Patent No. 3,785,136 discloses a radiotherapy apparatus in which a treatment plan can be scheduled easily after the radiotherapy is performed on a specimen. The radiotherapy apparatus includes a radiation irradiating head that irradiates therapeutic radiation; an image processing unit that generates images of the affected site of the specimen to which the therapeutic radiation is irradiated from the radiation irradiating head; and a controller that controls the radiation irradiating head and the image processing unit to repeat a period that includes periods for the generation of the image and the irradiation of the therapeutic radiation, and to generate the image of the affected site after ending the imaging of the image in which prior to the irradiation of the therapeutic radiation in a first period, a diagnostic X-ray is used in a second period following the first period, and after ending a process of the image during the irradiation of the therapeutic radiation in the first period.

DISCLOSURE OF THE INVENTION

A subject matter of the present invention is to provide a radiotherapy apparatus control apparatus and a specific site location measuring method, in which a specific site inside a specimen is measured with higher precision.

Another subject matter of the present invention is to provide a radiotherapy apparatus control apparatus and a specific site location measuring method, in which a template for measuring a specific site inside the specimen is properly generated.

Still another subject matter of the present invention is to provide a radiotherapy apparatus control apparatus and a specific site location measuring method, in which a template for measuring the specific site inside the specimen is generated more easily.

The radiotherapy apparatus control apparatus according to the present invention includes: a matching degree calculating section configured to calculate a plurality of matching degrees based on each of a template set and a plurality of transmission images imaged by using radiation transmitting through a specimen; a selecting section configured to select a template transmission image from the plurality of transmission images based on the matching degrees; and a template generating section configured to add a new template, which is generated based on the template transmission image, to the template set. The plurality of matching degrees correspond to an event of selecting one template from the template set and an event of selecting one transmission image from the plurality of transmission images and each matching degree indicates a degree at which a portion of the transmission image is similar to the template. At this time, the transmission image of the specimen imaged at an optional time has a high probability that it matches to any template of the thus-generated templates, even when a position relation between a specific portion of the specimen and a portion thereof other than the specific portion is different. Therefore, the radiotherapy apparatus control apparatus can measure the specific site with higher precision.

The radiotherapy apparatus control apparatus according to the present invention preferably includes: an imaging section configured to image a location measurement transmission image from radiation transmitting through a specimen; a template matching section configured to perform pattern-matching of each of templates of the template set with the location measurement transmission image and selects an optimal template which is the most similar to a portion of the location measurement transmission image, from the template set; a location calculating section configured to calculate a location of a specific site based on the location measurement transmission image and the optimal template; a driving unit configured to control a driving unit to drive a radiation irradiating unit to the specimen based on the specific site location such that therapeutic radiation transmits through the specific site location; and an irradiating section configured to control the radiation irradiating unit to irradiate the therapeutic radiation.

The radiotherapy apparatus control apparatus according to the present invention further includes a display section configured to display on a display unit, a display image generated based on the plurality of matching degrees. The selecting section selects the template transmission image from the plurality of transmission images based on data inputted by an operation of an input unit. According to the radiotherapy apparatus control apparatus, a user can select the template transmission image on the basis of the plurality of matching degrees and can select the template transmission image more properly and more easily.

The display image is preferred to indicate an order of imaging of the plurality of transmission images.

The display image is preferred to indicate a location of a region, which is calculated through the template-matching using the template set, of each of the plurality of transmission images.

The display image is preferred to identify a first transmission image, having a relatively high matching degree, of the plurality of transmission images and second transmission images having relatively low matching degrees of the plurality of transmission images.

The display image is preferred to identify the first transmission image, which is used to generate the template of the template set, of the plurality of transmission images and the second transmission images, which are not used to generate the template, of the plurality of transmission images.

The new template is preferred to indicate a template region image extracted from the template transmission image, based on data inputted by an operation of the input unit.

The template transmission image includes: a first template transmission image imaged by using the radiation irradiated from a first location; and a second template transmission image imaged by using radiation irradiated from a second location different from the first location. The new template includes: a first template for a first template region extracted from the first template transmission image; and a second template for a second template region extracted from the second template transmission image. The second template region is preferred to be extracted such that a location of the second template region in a predetermined direction corresponds to a location of the first template region in a predetermined direction.

A specific site location measuring method according to the present invention is achieved by calculating matching degrees based on a plurality of transmission images imaged by using radiation transmitting through a specimen and a template set; by selecting a template transmission image from the plurality of transmission images based on the matching degrees; by adding a new template generated based on the template transmission image, to the template set; by imaging a location measurement transmission image by using radiation transmitting through the specimen; by selecting an optimal template that is the most similar to a portion of the location measurement transmission image, from the template set by performing pattern matching between each of templates of the template set with the location measurement transmission image; and by calculating a specific site location based on the location measurement transmission image and the optimal template. Each of the matching degrees corresponds to selecting one of the templates from the template set and selecting a portion of one of the plurality of transmission images, and the matching degree indicates a degree at which a portion of the transmission image is similar to the template. At this time, the transmission image of the specimen imaged at an optional time has a high probability at which it matches with any template of the thus-generated templates, even when the location relation between the specific site of the specimen and the sites other than the specific site is different. Therefore, in the specific site location measuring method, the specific site can be measured with higher precision.

The specific site location measuring method according to the present invention further includes a display section for displaying on a display unit, a display image generated based on the plurality of matching degrees. The selecting section selects the template transmission image from the plurality of transmission images based on data inputted through the operation of the input unit. According to the specific site location measuring method, a user can select the template transmission image based on the plurality of matching degrees and can select the template transmission image more properly and more easily.

The display image is preferred to indicate an order of imaging of the plurality of transmission images.

The display image is preferred to indicate the locations calculated by the template matching of each of the plurality of transmission images to the template set.

The display image is preferred to identify a first transmission image, in which the matching degree is relatively high, of the plurality of transmission images and a second screen, in which the matching degree is relatively low, of the plurality of transmission images.

The display image is preferred to identify the first transmission image, which is used to generate the template of the template set, of the plurality of transmission images and second transmission images that are not used to generate the template of the plurality of transmission images.

The new template is preferred to indicate an image portion of the template region extracted from the template transmission image based on data inputted by an operation of the input unit.

A group of the template transmission images includes: a first template transmission image imaged by using radiation irradiated at a first location; and a second template transmission image imaged by using radiation irradiated at a second location different from the first location at a same time as the first template transmission image is imaged. The new template includes: a first template for a first template region extracted from the first template transmission image; and a second template for the second template region extracted from the second template transmission image. The second template region is extracted such that a location of the second template region in a predetermined direction corresponds to a location of the first template region in the predetermined direction.

The plurality of transmission images include the location measurement transmission image. That is, the specific site location measuring method according to the present invention can also generate a template by using the location measurement transmission image imaged in order to measure a specific site location.

A radiation irradiating method according to the present invention includes: a step of executing the specific site location measuring method according to the present invention; a step of controlling a driving unit, which drives a radiation irradiating unit for irradiating therapeutic radiation to a specimen based on the location so that the therapeutic radiation has transmitted through the specific site location; and a step of controlling the radiation irradiating unit to irradiate the therapeutic radiation. That is, the specific site location measuring method according to the present invention is preferred to be applied to the radiation irradiating method of irradiating the therapeutic radiation to the specific site location.

The radiotherapy apparatus control apparatus and the specific site location measuring method according to the present invention can generate the plurality of templates more properly and can measure the specific site inside the specimen with higher precision by using the plurality of templates.

BEST MODE FOR CARRYING OUT THE INVENTION

Figure 1:
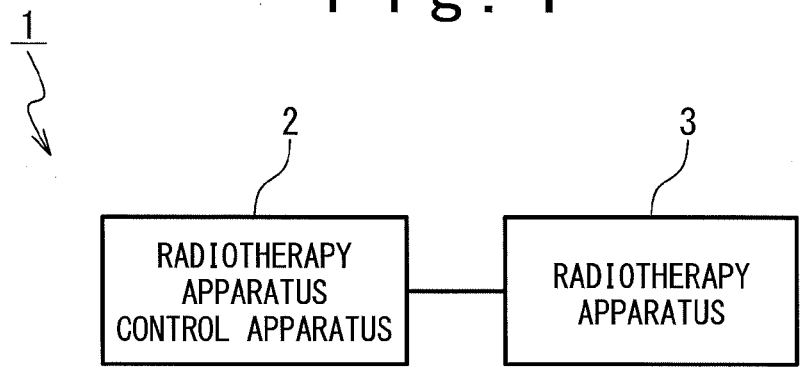
FIG. 1 is a block diagram showing a radiotherapy system.

A radiotherapy apparatus control apparatus according to embodiments of the present invention will be described below with reference to the attached drawings. The radiotherapy apparatus control apparatus 2 is applied to a radiotherapy system 1, as shown in FIG. 1. The radiotherapy system 1 includes the radiotherapy apparatus control apparatus 2 and a radiotherapy apparatus 3. The radiotherapy apparatus control apparatus 2 is exemplified as a personal computer. The radiotherapy apparatus control apparatus 2 and the radiotherapy apparatus 3 are connected to each other so that data can be bi-directionally transmitted.

Figure 2:
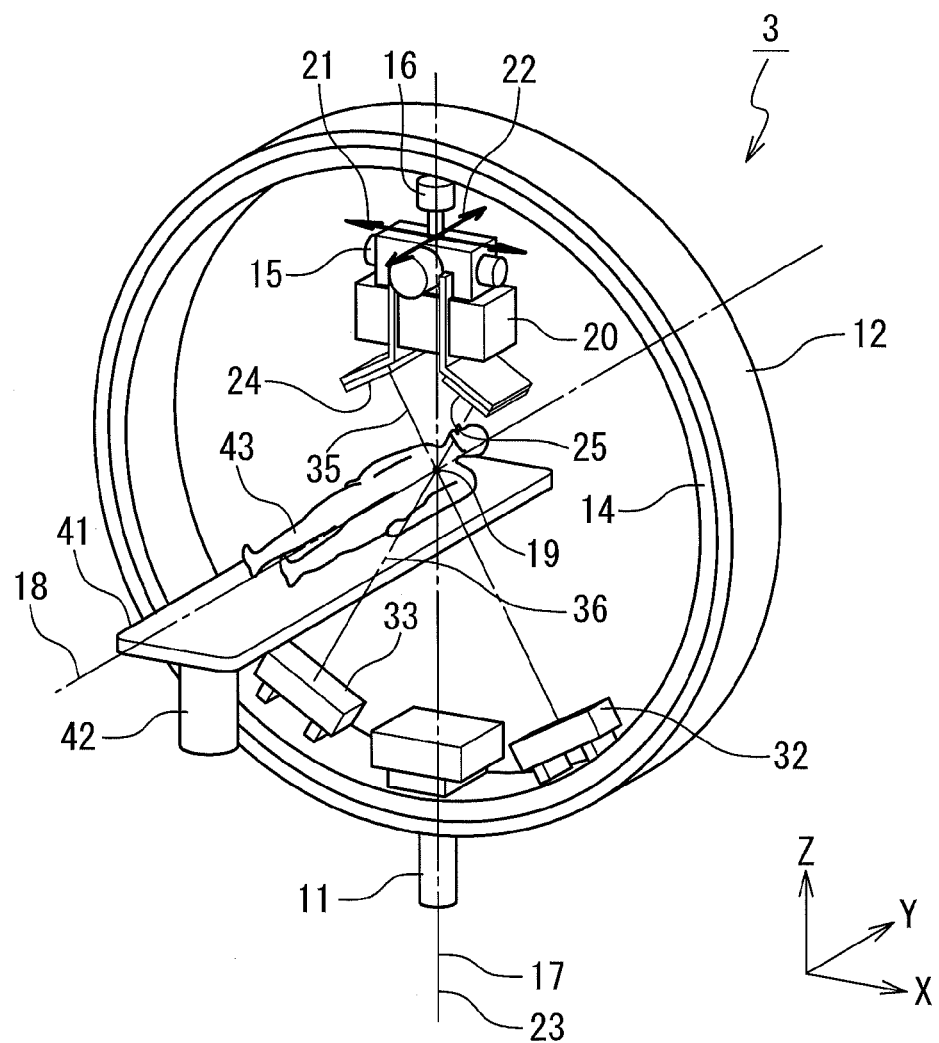
FIG. 2 is a perspective view showing the radiotherapy apparatus according to the present invention.

FIG. 2 shows the radiotherapy apparatus 3. The radiotherapy apparatus 3 includes a rotation driving unit 11, an O-ring 12, a travelling gantry 14, a swing mechanism 15 and a therapeutic radiation irradiating unit 16. The rotation driving unit 11 rotatably supports an O-ring 12 on a base and rotates the O-ring 12 around the rotation axis 17 under the control of the radiotherapy apparatus control apparatus 2. The rotation axis 17 is parallel to a vertical direction. The rotation driving unit 11 further measures a rotation angle of the O-ring 12 with respect to the base. The O-ring 12 is formed in the shape of a ring to have a rotation axis 18 and rotatably supports the travelling gantry 14 around the rotation axis 18. The rotation axis 18 is orthogonal to the vertical direction and passes through an isocenter 19 included in the rotation axis 17. The rotation axis 18 is fixed to the O-ring 12, that is, is rotated together with the O-ring 12 around the rotation axis 17. The travelling gantry 14 is formed in the shape of a ring with the rotation axis 18 and arranged concentrically with the ring of the O-ring 12. The radiotherapy apparatus 3 further includes a travelling driving unit that is not shown. The travelling driving unit rotates the travelling gantry 14 around the rotation axis 18 under the control of the radiotherapy apparatus control apparatus 2. The travelling driving unit further measures a travelling angle of the travelling gantry 14 with respect to the O-ring 12.

The swing mechanism 15 supports the therapeutic radiation irradiating unit 16 on the travelling gantry 14 so that the therapeutic radiation irradiating unit 16 is arranged inside the travelling gantry 14. The swing mechanism 15 has a tilt axis 21 and a pan axis 22. The pan axis 22 is fixed to the travelling gantry 14 and is parallel to the rotation axis 18 without intersecting the rotation axis 18. The tilt axis 21 is orthogonal to the pan axis 22. Under the control of the radiotherapy apparatus control apparatus 2, the swing mechanism 15 swings the therapeutic radiation irradiating unit 16 around the pan axis 22 and swings the therapeutic radiation irradiating unit 16 around the tilt axis 21.

The therapeutic radiation irradiating unit 16 irradiates therapeutic radiation 23 under the control of the radiotherapy apparatus control apparatus 2. The therapeutic radiation 23 is irradiated substantially along a straight line that passes through an intersection between the pan axis 22 and the tilt axis 21. The therapeutic radiation 23 is generated to have a uniform intensity distribution. The therapeutic radiation irradiating unit 16 includes a multi-leaf collimator (MLC) 20. Under the control of the radiotherapy apparatus control apparatus 2, the multi-leaf collimator 20 shields a part of the therapeutic radiation 23 and consequently controls the shape of an irradiation field when the therapeutic radiation 23 is irradiated to a patient.

Since the therapeutic radiation irradiating unit 16 is supported by the travelling gantry 14 as mentioned above, the therapeutic radiation 23 is always substantially passed through the isocenter 19, even if the O-ring 12 is rotated by the rotation driving unit 11, or even if the travelling gantry 14 is rotated by the travelling driving unit, once the therapeutic radiation irradiating unit 16 is adjusted to face the isocenter 19 by the swing mechanism 15. That is, the travelling and the rotation allow the therapeutic radiation 23 to be irradiated to the isocenter 19 from any direction.

The radiotherapy apparatus 3 further includes a plurality of imager systems. That is, the radiotherapy apparatus 3 includes diagnostic X-ray sources 24 and 25 and sensor arrays 32 and 33. The diagnostic X-ray source 24 is supported by the travelling gantry 14. The diagnostic X-ray source 24 is arranged inside the ring of the travelling gantry 14 such that an angle between a line passing through the diagnostic X-ray source 24 and the isocenter 19 and a line passing through the therapeutic radiation irradiating unit 16 and the isocenter 19 is acute. The diagnostic X-ray source 24 emits a diagnostic X-ray 35 to the isocenter 19 under the control of the radiotherapy apparatus control apparatus 2. The diagnostic X-ray 35 is irradiated in the form of a conical cone beam from one point of the diagnostic X-ray source 24. The diagnostic X-ray source 25 is supported by the travelling gantry 14. The diagnostic X-ray source 25 is arranged inside the ring of the travelling gantry 14 such that an angle between a line passing through the diagnostic X-ray source 25 and the isocenter 19 and a line passing through the therapeutic radiation irradiating unit 16 and the isocenter 19 is acute. The diagnostic X-ray source 25 emits a diagnostic X-ray 36 to the isocenter 19 under the control of the radiotherapy apparatus control apparatus 2. The diagnostic X-ray 36 is irradiated in the form of a conical cone beam from one point of the diagnostic X-ray source 25.

The sensor array 32 is supported by the travelling gantry 14. The sensor array 32 receives the diagnostic X-ray 35, which is irradiated from the diagnostic X-ray source 24 and has transmitted through a portion of a specimen around the isocenter 19, and generates an image signal for a transmission image of the specimen. The sensor array 33 is supported by the travelling gantry 14. The sensor array 33 receives the diagnostic X-ray 36, which is irradiated from the diagnostic X-ray source 25 and has transmitted through a portion of the specimen around the isocenter 19, and generates an image signal for a transmission image of the specimen. As the sensor arrays 32 and 33, FPD (Flat Panel Detector) and an X-ray II (Image Intensifier) are exemplified.

According to such an imager system, the transmission images around the isocenter 19 can be generated from the image signals sensed by the sensor arrays 32 and 33.

The radiotherapy apparatus 3 further includes a couch 41 and a couch driving unit 42. The couch 41 is used for a patient 43 to lie for treat by use of the radiotherapy system 1. The couch 41 includes a fixing tool (not shown). The fixing tool fixes the patient to the couch 41 so that the patient cannot move. The couch driving unit 42 supports the couch 41 on the base and moves the couch 41 under the control of the radiotherapy apparatus control apparatus 2.

Figure 3:
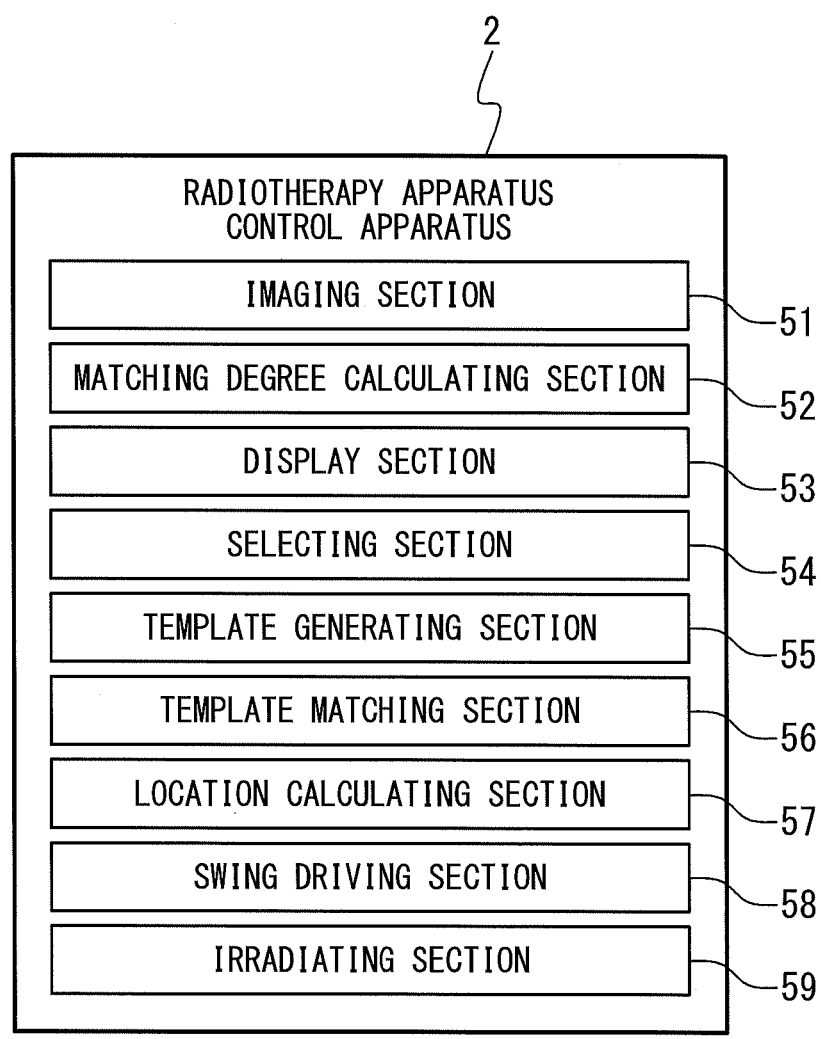
FIG. 3 is a block diagram showing a radiotherapy apparatus control apparatus.

FIG. 3 shows a configuration of the radiotherapy apparatus control apparatus 2. The radiotherapy apparatus control apparatus 2 includes a CPU, a storing unit, an input unit and an interface, which are not shown. The CPU executes a computer program installed in the radiotherapy apparatus control apparatus 2 from a tangible recording medium and controls the storing unit, the input unit and the interface. The storing unit records the computer program and temporarily records data generated by the CPU. The input unit generates input data when it is operated by the user, and outputs the input data to the CPU. As the input unit, a keyboard and a pointing device are exemplified. The interface outputs to the CPU, data which are generated by external units connected to the radiotherapy apparatus control apparatus 2, and outputs data generated by the CPU to the external units. The external units includes the rotation driving unit 11, the travelling driving unit, the swing mechanism 15, the therapeutic radiation irradiating unit 16, the multi-leaf collimator 20, the imager systems (the diagnostic X-ray sources 24 and 25 and the sensor arrays 32 and 33) and the couch driving unit 42 in the radiotherapy apparatus 3.

The computer program realizes an imaging section 51, a matching degree calculating section 52, a display section 53, a selecting section 54, a template generating section 55, a template matching section 56, a location calculating section 57, a swing driving section 58 and an irradiating section 59.

The imaging section 51 uses the diagnostic X-ray source 24 and the sensor array 32 to generate a plurality of first transmission images at a plurality of times, which differ from each other, respectively, and also uses the diagnostic X-ray source 25 and the sensor array 33 to generate a plurality of second transmission images at the plurality of times. Moreover, during the radiotherapy, the imaging section 51 uses the diagnostic X-ray source 24 and the sensor array 32 to generate a first location measurement transmission image of the patient 43 and simultaneously uses the diagnostic X-ray source 25 and the sensor array 33 to generate a second location measurement transmission image of the patient 43.

The matching degree calculating section 52 calculates a plurality of matching degrees on the basis of the plurality of first transmission images and the plurality of second transmission images, which are acquired by the imaging section 51, and a plurality of first templates which are generated by the template generating section 55.

The display section 53 generates a matching result data on the basis of the plurality of matching degrees calculated by the matching degree calculating section 52 and displays the matching result data on a display unit.

On the basis of data inputted from the input unit, the selecting section 54 selects a plurality of first template generation transmission images from the plurality of first transmission images acquired by the imaging section 51 and selects a plurality of second template generation transmission images from the plurality of second transmission images acquired by the imaging section 51.

The template generating section 55 generates the plurality of first templates from the plurality of first template generation transmission images selected by the selecting section 54, on the basis of data inputted from the input unit, respectively. The template generating section 55 generates the plurality of second templates from the plurality of second template generation transmission images selected by the selecting section 54, on the basis of data inputted from the input unit, respectively.

The template matching section 56 calculates a first location on the basis of the first location measurement transmission image acquired by the imaging section 51 during the radiotherapy and the plurality of first templates generated by the template generating section 55. The template matching section 56 further calculates a second location on the basis of a second location measurement transmission image acquired by the imaging section 51 during the radiotherapy and the plurality of second templates generated by the template generating section 55.

The location calculating section 57 calculates an affected site location of the patient 43 on the basis of the first location and the second location that are calculated by the template matching section 56. The swing driving section 58 drives the therapeutic radiation irradiating unit 16 by using the swing mechanism 15 so that the therapeutic radiation 23 transmits through the affected site location calculated by the location calculating section 57. The irradiating section 59 calculates the shape of the irradiation field on the basis of the transmission images acquired by the imaging section 51, and controls the multi-leaf collimator 20 so that the irradiation field of the therapeutic radiation 23 is formed on the basis of the calculated shape. The irradiating section 59 uses the therapeutic radiation irradiating unit 16 to irradiate the therapeutic radiation 23 to the patient.

Figure 4:
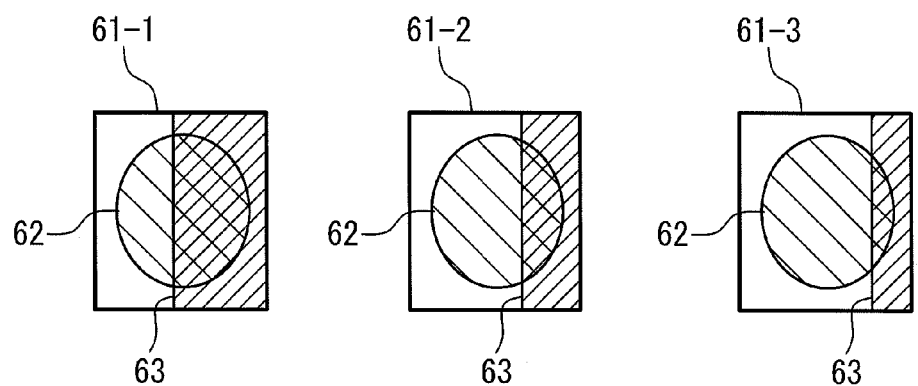
FIG. 4 is a diagram showing templates.

FIG. 4 shows examples of the plurality of templates generated by the template generating section 55. An affected site 62 and a bone 63 of the patient 43 are depicted on each of templates 61-1 to 61-3, respectively. The locations at which the affected site 62 is depicted are same on the templates 61-1 to 61-3. The locations at which the bone 63 is depicted are different from each other on the templates 61-1 to 61-3.

Figure 5:
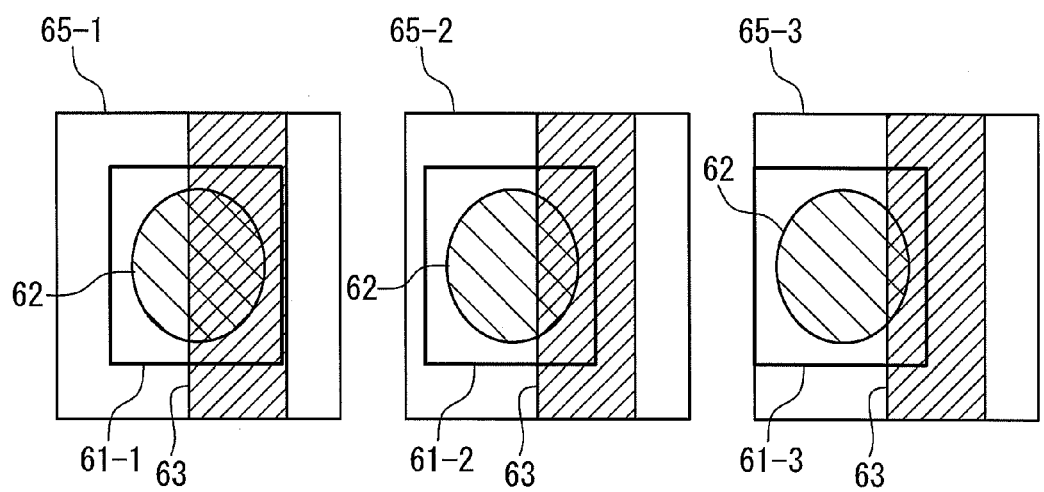
FIG. 5 is a diagram showing transmission images.

FIG. 5 shows examples of the plurality of first transmission images acquired by the imaging section 51 at the plurality of times that differ from each other. The phases of the breathings of the patient 43 at the plurality of times differ from each other. The affected site 62 and the bone 63 of the patient 43 are depicted on each of a plurality of transmission images 65-1 to 65-3. The locations at which the affected site 62 or the bone 63 is depicted are different from each other on the plurality of transmission images 65-1 to 65-3. Moreover, the position relations between the affected site 62 and the bone 63 that are depicted on the plurality of transmission images 65-1 to 65-3 are different from each other.

At this time, the matching degree calculating section 52 determines the location of a region in the transmission image 65-1, which region is the most similar to the template 61-1, and calculates the matching degree at the determined location. The matching degree indicates at what degree the region is similar to the image template and indicates that as the value is higher, the region is more similar to the image template. As a pattern matching image processing method, an optical flow method, and a high speed template matching method based on monotonic functioning of a normalized correlation operation are exemplified. As the optical flow method, a slop method and a block matching method are exemplified.

Then, the matching degree calculating section 52 calculates the location of the most similar region and the matching degree at the location, for each of the other templates 61-2 to 61-3, similarly to the template 61-1. Next, the matching degree calculating section 52 determines the template 61-1 in which the maximum matching degree is calculated from among the plurality of matching degrees calculated with regard to the transmission image 65-1, and calculates the location of the region in the transmission image 65-1 which region is the most similar to the template 61-1, and then calculates the matching degree of the region. Similarly to the transmission image 65-1, the matching degree calculating section 52 calculates the most similar template to each of the plurality of templates 61-1 to 61-3 from each of the transmission images 65-2 to 65-3, and calculates the location of the region that is the most similar to the template and then calculates the matching degree.

Similarly to the matching degree calculating section 52, the template matching section 56 calculates the most similar template to the first location measurement transmission image acquired by the imaging section 51 from among the plurality of first templates generated by the template generating section 55, and calculates a first location of the region that is the most similar to the template and then calculates a first matching degree. Moreover, the template matching section 56 calculates the most similar template to the second location measurement transmission image acquired by the imaging section 51 from among the plurality of second templates generated by the template generating section 55, and calculates a second location of the region that is the most similar to the template and then calculates a second matching degree. When the first matching degree is higher than a threshold and the second matching degree is higher than the threshold, the location calculating section 57 calculates the location of the affected site of the patient 43 on the basis of the first location and the second location. When the first matching degree is lower than a threshold, or when the second matching degree is lower than the threshold, the location calculating section 57 does not calculate the location of the affected site of the patient 43.

Figure 6:
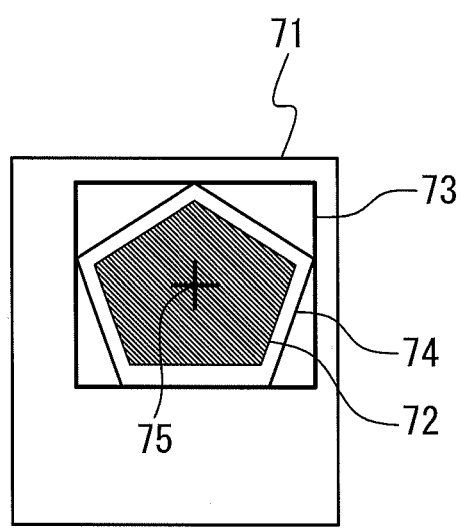
FIG. 6 is a diagram showing a matching result display image generated by a display section.

FIG. 6 shows a matching result display on the display section 53. The matching result display 71 represents one among the plurality of first transmission images acquired by the imaging section 51. An affected site 72 of the patient 43 is depicted on the transmission image. The matching result display further represents a frame 73, a PTV projection 74 and a cross 75 so as to superimpose on the transmission image. The frame 73 is displayed in the location of the region on the transmission image calculated by the matching degree calculating section 52. The PTV projection 74 corresponds to a region in which a three-dimensional irradiation region (PTV, Planning Tumor Volume) of the affected site of the patient 43 is projected, and is displayed in the location corresponding to the location of the region calculated by the matching degree calculating section 52, on the transmission image. The cross 75 corresponds to a feature point of the affected site of the patient 43, and is displayed in the location corresponding to the location of the region calculated by the matching degree calculating section 52, on the transmission image. As the feature point, the center of the gravity of the affected site is exemplified.

The display section 53 displays any one transmission image among the plurality of first transmission images acquired by the imaging section 51 for the above matching result display on the basis of data from the input unit.

According to such a matching result display, the user can easily determines whether or not the template is template-matched on a proper location of the transmission image, on the basis of the relation between location at which the affected site 72 is displayed and the location on which the frame 73, the PTV projection 74 or the cross 75 is displayed.

Figure 7:
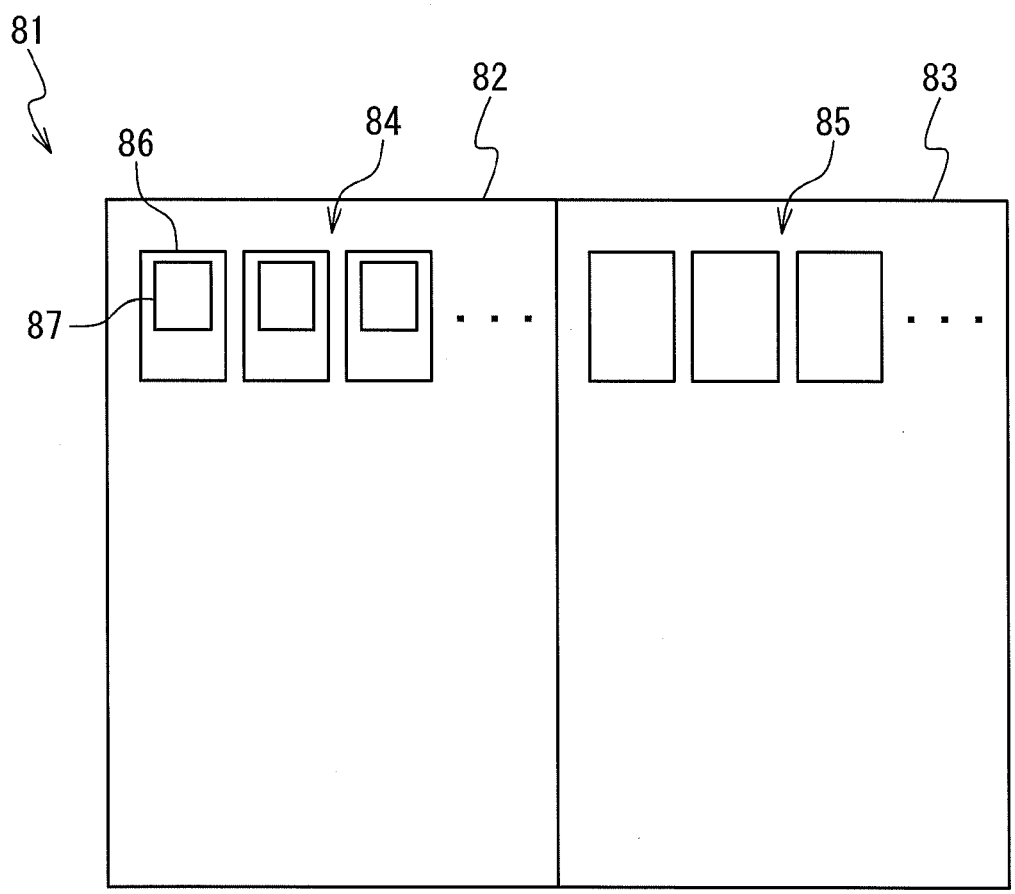
FIG. 7 is a diagram showing another matching result display image generated by the display section.

FIG. 7 shows another matching result display performed by the display section 53. The matching result display 81 includes a first region 82 and a second region 83. A plurality of transmission images 84 are displayed in the first region 82. The plurality of transmission images 84 include transmission images from which the matching degrees higher than a predetermined threshold are calculated by the matching degree calculating section 52. A frame 87 is displayed on each of the plurality of transmission images 84. The frame 87 is displayed in the location of the region calculated by the matching degree calculating section 52 for each of the transmission images 84. Another plurality of transmission images 85 from which the matching degrees lower than the threshold are calculated by the matching degree calculating section 52 are displayed in the second region 83.

The matching result display 81 indicates the state of the affected site of the patient 43*a* when the template matching is not properly performed. For this reason, a user can easily check a template to be added to indicate the above state of the affected site of the patient 43, by referring to the matching result display 81.

Figure 8:
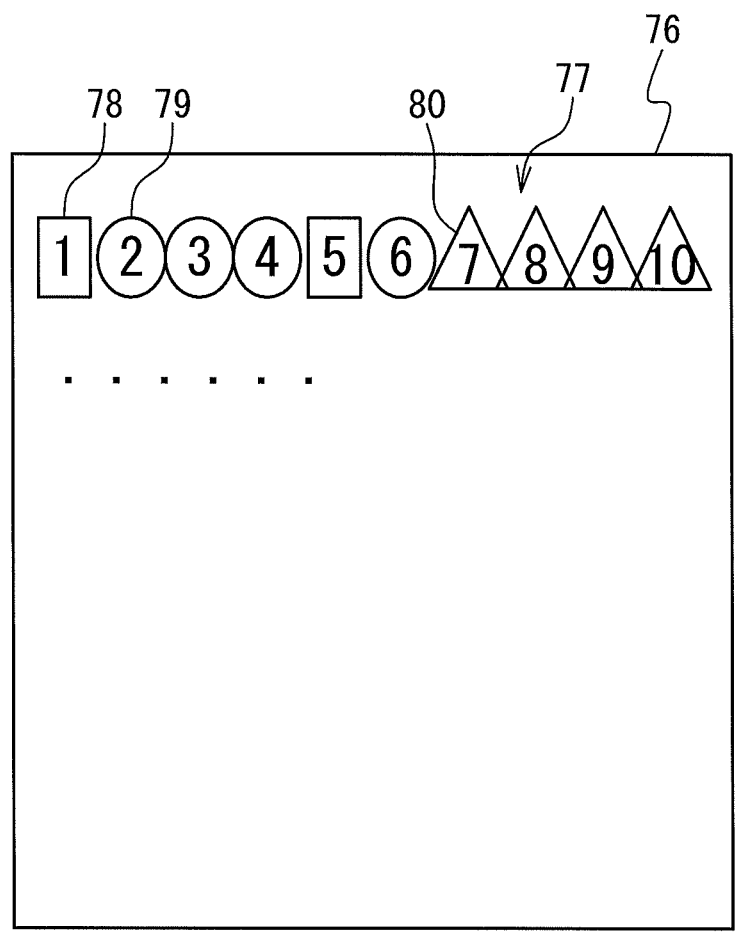
FIG. 8 is a diagram showing still another matching result display image generated by the display section.

FIG. 8 shows still another matching result display on the display section 53. The matching result display 76 displays a plurality of image numbers 77. The plurality of image numbers 77 correspond to the plurality of first transmission images acquired by the imaging section 51, respectively, and identify the plurality of first transmission images. The plurality of image numbers 77 are arranged in a matrix, and an order at which the plurality of image numbers 77 are arranged coincides with an order at which the plurality of first transmission images are imaged. Each of the plurality of image numbers 77 includes a first image number 78, a second image number 79 and a third image number 80. The first image number 78 is displayed in a first display mode. The first transmission image corresponding to the first image number 78 is used to generate the first template by the template generating section 55. The second image number 79 is displayed in a second display mode different from the first display mode. In the first transmission image corresponding to the second image number 79, the matching degree higher than the predetermined threshold is calculated by the matching degree calculating section 52. The third image number 80 is displayed in a third display mode that differs from the first display mode and also differs from the second display mode. In the first transmission image corresponding to the third image number 80, the matching degree lower than a predetermined threshold is calculated by the matching degree calculating section 52.

The matching result display 76 indicates a timing at which the transmission image that is not properly template-matched is imaged. For this reason, the user can easily check a template which is generated from the transmission image imaged at the above timing and is to be added, by referring to the matching result display 76.

Figure 9:
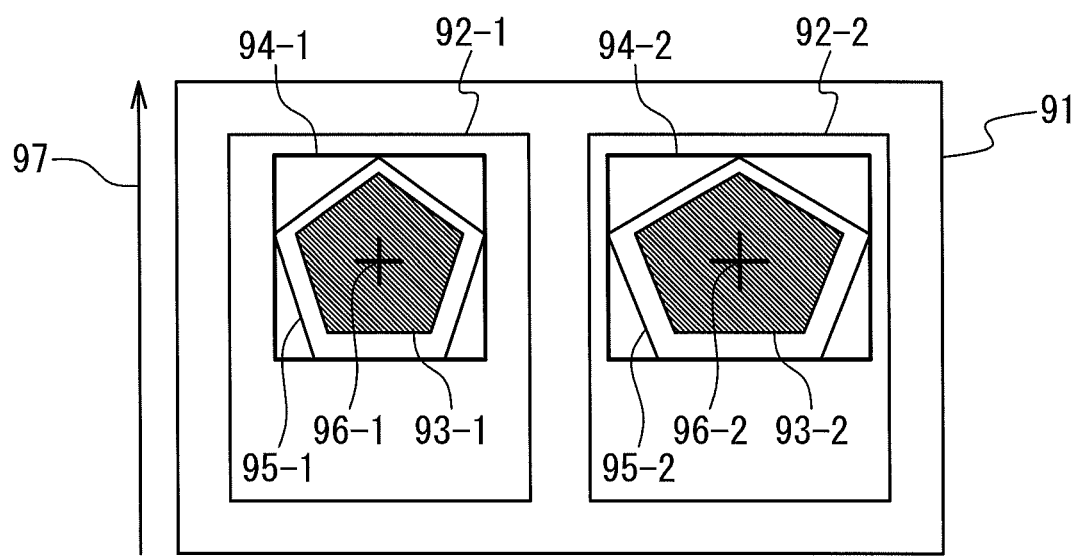
FIG. 9 is a diagram showing a display image when template regions are specified.

FIG. 9 shows a display on the display unit when the template generating section 55 generates the first template and the second template. The display 91 represents a first template generation transmission image 92-1 and a second template generation transmission image 92-2. The first template generation transmission image 92-1 indicates one of a plurality of first template generation transmission images selected by the selecting section 54, and depicts an image 93-1 of the affected site of the patient 43. The second template generation transmission image 92-2 indicates an image, which is imaged simultaneously with the first template generation transmission image 92-1 in a plurality of second template generation transmission images selected by the selecting section 54, and depicts the image 93-1 of the affected site of the patient 43.

In the display 91, a frame 94-1, a PTV projection 95-1 and a cross 96-1 are further displayed to be superimposed on the first template generation transmission image 92-1. The frame 94-1 is displayed in the location of the region calculated from the first template generation transmission image 92-1 by the matching degree calculating section 52. The PTV projection 95-1 corresponds to the region to which the three-dimensional irradiation field (PTV) of the affected site of the patient 43 is projected, and this is displayed in the location corresponding to the location of the region calculated from the first template generation transmission image 92-1 by the matching degree calculating section 52. The cross 96-1 corresponds to a feature point of the affected site of the patient 43, and this is displayed in the location corresponding to the location of the region calculated from the first template generation transmission image 92-1 by the matching degree calculating section 52.

On the screen 91, a frame 94-2, a PTV projection 95-2 and a cross 96-2 are further displayed to be superimposed on the second template generation transmission image 92-2. The frame 94-2 is displayed in the location in the region calculated from the second template generation transmission image 92-2 by the matching degree calculating section 52. The PTV projection 95-2 corresponds to the region to which the 3-dimensional irradiation field (PTV) of the affected site of the patient 43 is projected, and this is displayed in the location corresponding to the location of the region calculated from the second template generation transmission image 92-2 by the matching degree calculating section 52. The cross 96-2 corresponds to the feature point of the affected site of the patient 43, and this is displayed in the location corresponding to the location of the region calculated from the second template generation transmission image 92-2 by the matching degree calculating section 52.

The template generating section 55 changes the location in which the frame 94-1 is displayed, on the basis of data inputted from the input unit. At this time, the template generating section 55 further changes the locations in which the frame 94-1, the PTV projection 95-1 and the cross 96-1 are displayed, such that the position relation between the frame 94-1, the PTV projection 95-1 and the cross 96-1 is not changed. The template generating section 55 further changes the locations in which the frame 94-1 and the frame 94-2 are displayed, such that the location of the frame 94-1 in a direction 97 coincides with the location of the frame 94-2 in the direction 97.

The template generating section 55 changes the location in which the frame 94-2 is displayed, on the basis of data inputted from the input unit. At this time, the template generating section 55 further changes the locations in which the frame 94-2, the PTV projection 95-2 and the cross 96-2 are displayed, such that the position relation between the frame 94-2, the PTV projection 95-2 and the cross 96-2 is not changed. The template generating section 55 further changes the locations in which the frame 94-2 and the frame 94-1 are displayed, in such a way that the location of the frame 94-2 in the direction 97 coincides with the location of the frame 94-1 in the direction 97.

After the location of the frame 94-1 or frame 94-2 is changed on the basis of the data inputted from the input unit, the template generating section 55 generates the first template on the basis of the first template generation transmission image 92-1 and generates the second template on the basis of the second template generation transmission image 92-2. The first template coincides with an image portion, which is displayed in the region surrounded by the frame 94-1, of the first template generation transmission image 92-1. The second template coincides with the image portion, which is displayed in the region surrounded by the frame 94-2, of the second template generation transmission image 92-2.

The location of the image 93-1 of the affected site of the patient 43 in the direction 97 in the first template generation transmission image 92-1 coincides with the location of the image 93-2 of the affected site in the direction 97 in the second template generation transmission image 92-2. For this reason, the operation of the user can be made easy when the template generating section 55 generates the first template and the second template from the first template generation transmission image 92-1 and the second template generation transmission image 92-2.

The irradiating method according to the present embodiment is performed by using the radiotherapy system 1 and includes an operation of generating the templates, an operation of performing the radiotherapy and an operation of modifying the template.

Figure 10:
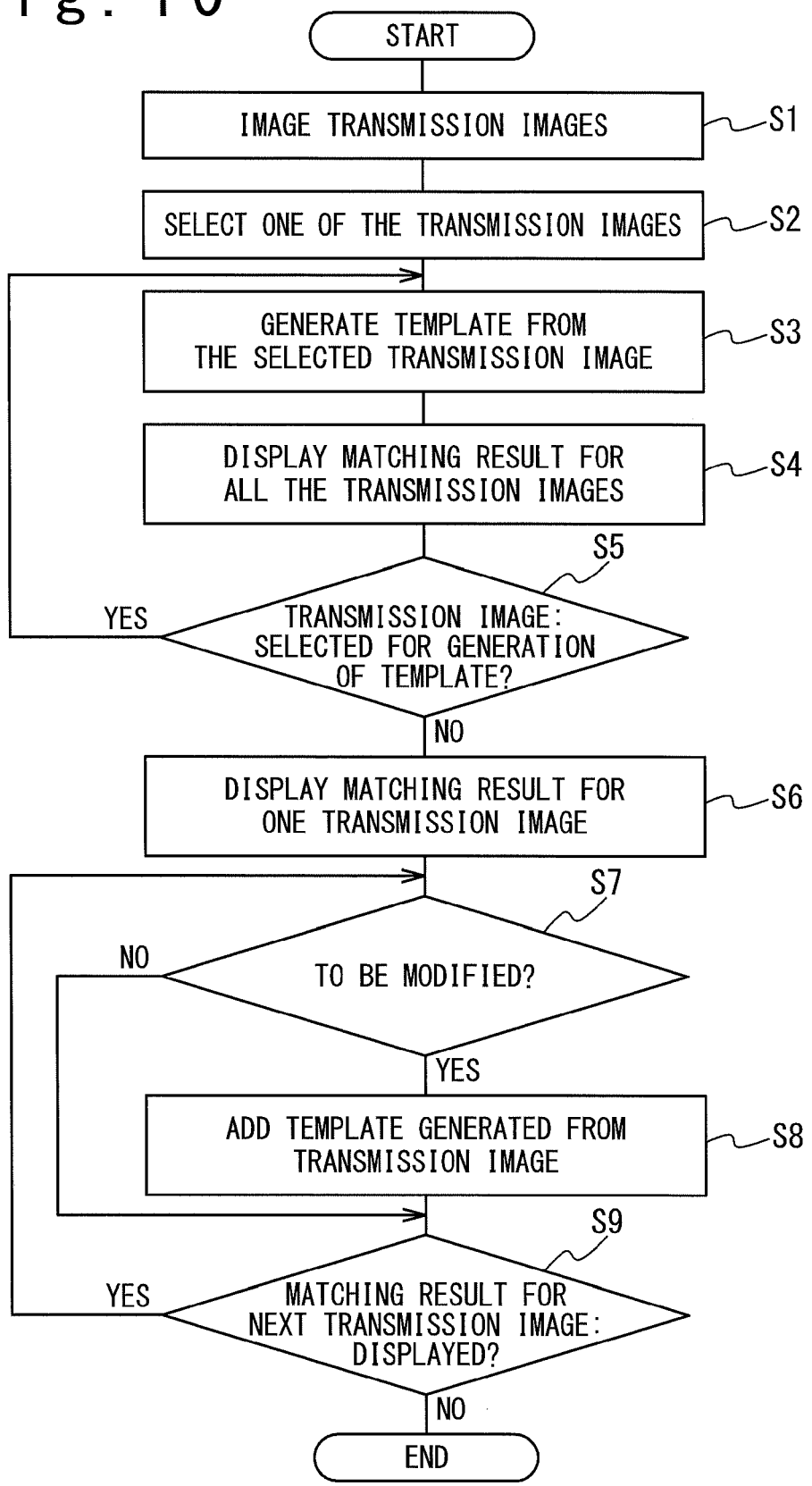
FIG. 10 is a flowchart showing an operation of generating a template.

FIG. 10 shows the operation of generating a template. The user first fixes the patient 43 onto the couch 41 of the radiotherapy apparatus 3. Moreover, the user operates the radiotherapy apparatus control apparatus 2 to move the couch 41 in such a way that the affected site of the patient 43 is arranged to substantially overlap the isocenter 19. The radiotherapy apparatus control apparatus 2 fixes the O-ring 12 at a predetermined rotation angle by using the rotation driving unit 11 of the radiotherapy apparatus 3 and fixes the travelling gantry 14 at a predetermined travel angle by using the travelling driving unit of the radiotherapy apparatus 3 such that the therapeutic radiation 23 is irradiated to the affected site of the patient 43 in an irradiation angle indicated by a therapy plan. The radiotherapy apparatus control apparatus 2 controls the diagnostic X-ray source 24 and the sensor array 32 to image the plurality of first transmission images of the patient 43 at a plurality of imaging times different from each other, and the diagnostic X-ray source 25 and the sensor array 33 to image a plurality of second transmission images of the patient 43 at the plurality of imaging times in a situation that the travelling gantry 14 is fixed (Step S1).

The user selects a proper one of the plurality of first transmission images and inputs data from the input unit into the radiotherapy apparatus control apparatus 2 to identify the selected first transmission image. The radiotherapy apparatus control apparatus 2 displays the selected first transmission image on the display unit. The radiotherapy apparatus control apparatus 2 further extracts one second transmission image imaged simultaneously with the selected first transmission image from the plurality of second transmission images, and displays the extracted second transmission image on the display unit (Step S2).

The user views the displayed first transmission image, and extracts a region of the first template on the first transmission image, and then inputs data indicating the location of the region from the input unit into the radiotherapy apparatus control apparatus 2. The radiotherapy apparatus control apparatus 2 generates the first template having a region image of the extracted region. The user views the displayed second transmission image, and extracts a region of the second template from the second transmission image, and then inputs data indicating the location of the region, from the input unit into the radiotherapy apparatus control apparatus 2. The radiotherapy apparatus control apparatus 2 generates the second template having a region image of the extracted region (Step S3).

The radiotherapy apparatus control apparatus 2 calculates the location of the region which is the most similar to each of the first templates from each of the plurality of first transmission images, and then calculates a matching degree. Subsequently, the radiotherapy apparatus control apparatus 2 calculates one of the first templates corresponding to the maximum matching degree of the plurality of matching degrees calculated for each of the plurality of first transmission images, and calculates the location of the region, which is the most similar to the first template, from each of the plurality of first transmission images, and then calculates the matching degree. Like a case to the plurality of first transmission images, the radiotherapy apparatus control apparatus 2 calculates the location of a region, which is the most similar to each of the second templates, from each of the plurality of second transmission images, and calculates the matching degree. Subsequently, the radiotherapy apparatus control apparatus 2 calculates one of the second templates corresponding to the maximum matching degree of the plurality of matching degrees calculated for each of the plurality of second transmission images, and calculates the location of the region, which is the most similar to the second template, from each of the plurality of second transmission images, and then calculates the matching degree. The radiotherapy apparatus control apparatus 2 generates the matching result displays 71, 76 and 81, on the basis of the locations of the regions and the matching degrees which are calculated as mentioned above, and displays the matching result displays 71, 76 and 81 on the display unit (Step S4).

The user refers to the matching result displays 71, 76 and 81, and selects a proper first transmission image for the first template from the plurality of first transmission images, and then inputs data into the radiotherapy apparatus control apparatus 2 to identify the selected first transmission image (Step S5, Selection). At this time, the radiotherapy apparatus control apparatus 2 displays on the display unit, the display image 91 which is generated on the basis of the selected first transmission image and one second transmission image imaged simultaneously with the selected first transmission image (Step S2). On the basis of data inputted from the input unit, the radiotherapy apparatus control apparatus 2 generates the first template from the selected first transmission image and the second template from the selected second transmission image (Step S3). The radiotherapy apparatus control apparatus 2 adds the newly-generated first template and second template to the existing templates, and calculates the locations of the regions, which are the most similar to the templates with respect to the plurality of first transmission images and plurality of second transmission images, and the matching degrees. The radiotherapy apparatus control apparatus 2 generates the matching result displays 71, 76 and 81 on the basis of the locations of the regions and the matching degrees that are calculated as mentioned above, and displays the matching result displays 71, 76 and 81 on the display unit (Step S4). The above operation of the step S3 and step S4 is repeatedly executed until the user inputs data into the radiotherapy apparatus control apparatus 2 at the step S5 to indicate that the template is not generated any more.

When referring to the matching result displays 71, 76 and 81 and knowing that the enough number of the first templates are generated, the user inputs data to the radiotherapy apparatus control apparatus 2 to indicate that the first template is not generated any more (Step S5, No). At this time, the radiotherapy apparatus control apparatus 2 displays on the display unit, the display image 91 generated on the basis of the proper first transmission image of the plurality of first transmission images and the second transmission image imaged simultaneously with the proper first transmission image (Step S6).

When referring to the display 91 and knowing that the location of the template-matched region is required to be modified, the user inputs data indicating a proper location from the input unit into the radiotherapy apparatus control apparatus 2. When the location is modified (Step S7: Yes), the radiotherapy apparatus control apparatus 2 generates a first template corresponding to an image of the modified region in the first transmission image, and then generates a second template corresponding to an image of the modified region of the second transmission image (Step S8).

When the location is not modified (Step S7: No) or after the step S8 is executed, the radiotherapy apparatus control apparatus 2 displays the display 91 on the display unit on the basis of the first transmission image and the second transmission image imaged next to the first transmission image and the second transmission image (Step S9). When referring to the display 91 and knowing that the location of the template-matched region is required to be modified, the user inputs data indicating a proper location from the input unit into the radiotherapy apparatus control apparatus 2. When the location is modified (Step S7: Yes), the radiotherapy apparatus control apparatus 2 generates a first template corresponding to the modified region image of the first transmission image, and a second template corresponding to the modified region image of the second transmission image (Step S8). The operation from the step S7 to the step S9 is repeatedly executed, until it is confirmed that any modification is not required to any of the plurality of first transmission images and the plurality of second transmission images.

According to such an operation, the first template and the second template are generated such that all of the plurality of first transmission images and the plurality of second transmission images are properly template-matched. For this reason, by using the first template and second template thus generated, the radiotherapy system 1 can calculate the location of the affected site of the patient 43 with higher precision and can perform the radiotherapy on the patient 43 with the higher precision. According to such an operation, the user can easily recognize a type of required template and can easily generate the first template and the second template.

The operation of performing the radiotherapy may be performed in a state that the patient 43 is fixed, immediately after the operation of generating the templates. The radiotherapy apparatus control apparatus 2 controls the rotation driving unit 11 of the radiotherapy apparatus 3 and fixes the O-ring 12 at a rotation angle indicated by a therapy plan and also controls the travelling driving unit in the radiotherapy apparatus 3 and fixes the travelling gantry 14 at a travelling angle indicated by the therapy plan.

In the state that the travelling gantry 14 is fixed, the radiotherapy apparatus control apparatus 2 controls the diagnostic X-ray source 24 and the sensor array 32 to image a first location measurement transmission image of the patient 43 and also controls the diagnostic X-ray source 25 and the sensor array 33 to image a second location measurement transmission image of the patient 43. The radiotherapy apparatus control apparatus 2 determines the most similar template to the first location measurement transmission image from a plurality of first templates, and calculates a first location of a region that is the most similar to the determined template, and then calculates a first matching degree. Moreover, the radiotherapy apparatus control apparatus 2 determines the most similar template to the second location measurement transmission image from the plurality of second templates, and calculates a second location of a region that is the most similar to the determined template, and then calculates a second matching degree. When the first matching degree is higher than a threshold and the second matching degree is higher than the threshold, the radiotherapy apparatus control apparatus 2 calculates a location of the affected site of the patient 43 on the basis of the first location and the second location. When the first matching degree is lower than the threshold or when the second matching degree is lower than the threshold, the radiotherapy apparatus control apparatus 2 does not calculate the location of the affected site of the patient 43.

When the location of the affected site can be specified on the basis of the two transmission images, the radiotherapy apparatus control apparatus 2 displays on the display unit, data indicating that the location of the affected site has be specified. The radiotherapy apparatus control apparatus 2 further controls the swing mechanism 15 on the basis of the calculated location of the affected site such that an irradiation axis of the therapeutic radiation 23 is located at the affected site. The radiotherapy apparatus control apparatus 2 further calculates the shape of an irradiation field on the basis of the first location measurement transmission image and the second location measurement transmission image, and controls the multi-leaf collimator 20 such that the irradiation field of the therapeutic radiation 23 is formed based on the calculated shape. The radiotherapy apparatus control apparatus 2 further controls the therapeutic radiation irradiating unit 16 to irradiate the therapeutic radiation 23 to the patient.

When the location of the affected site cannot be specified, the radiotherapy apparatus control apparatus 2 displays data on the display unit to indicate that the location of the affected site cannot be specified.

The radiotherapy apparatus control apparatus 2 periodically performs such operations, until a dose of the therapeutic radiation 23 irradiated to the affected site of the patient 43 reaches a dose of the therapy plan.

When a period for which the location of the affected site cannot be specified is frequently generated, the user inputs data to the radiotherapy apparatus control apparatus 2 to instruct the stop of this repetition. The radiotherapy apparatus control apparatus 2 stops the operation of performing the radiotherapy in response to the input of the instruction.

Figure 11:
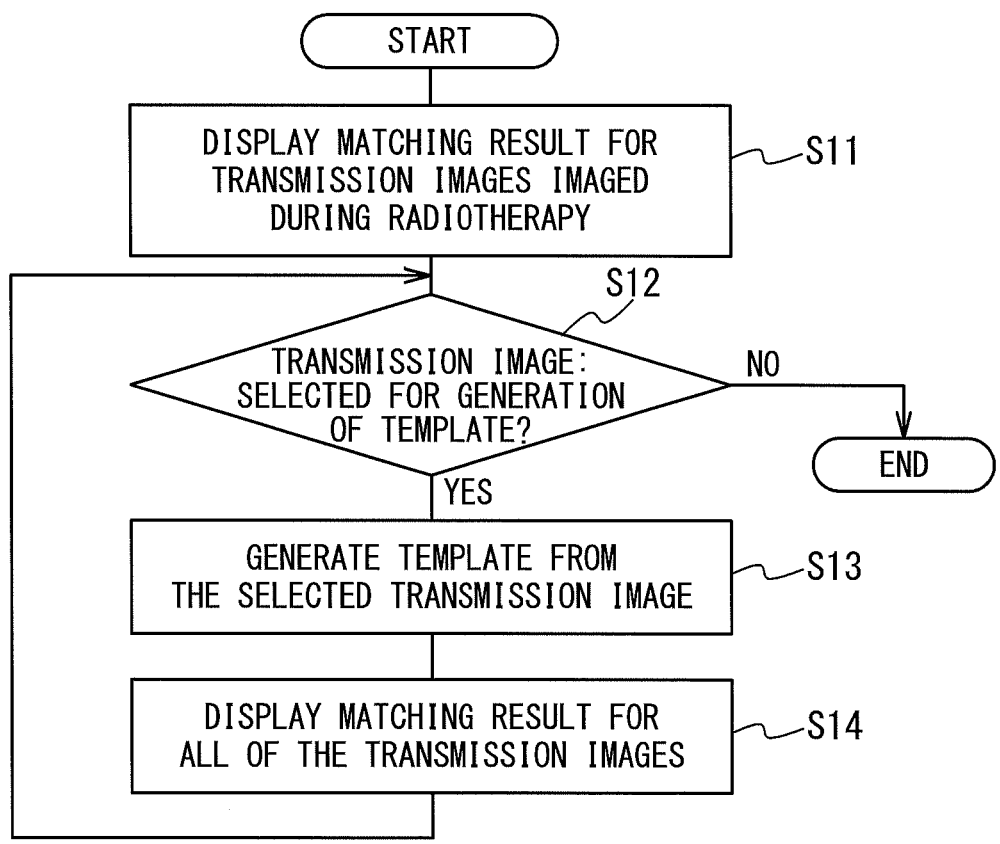
FIG. 11 is a flowchart showing an operation of modifying the template.

FIG. 11 shows an operation of modifying the template. The operation of modifying the template is performed when the operation of performing the radiotherapy is stopped by the user. The radiotherapy apparatus control apparatus 2 calculates the location of a region, which is the most similar to each of the first templates, from each of the plurality of first location measurement transmission images imaged during the radiotherapy and then calculates the matching degree. Subsequently, the radiotherapy apparatus control apparatus 2 calculates one of the first templates for the maximum matching degree of the plurality of matching degrees calculated with respect to each of the plurality of first transmission images, and then calculates the matching degree. Like the plurality of first transmission images, the radiotherapy apparatus control apparatus 2 calculates the location of a region, which is the most similar to each of the second templates, with respect to each of the plurality of second transmission images and then calculates the matching degree. Subsequently, the radiotherapy apparatus control apparatus 2 calculates one of the second templates for the maximum matching degree of the plurality of matching degrees calculated for each of the plurality of second transmission images, and calculates the location of the region, which is the most similar to one second template, with respect to each of the plurality of second transmission images, and the calculates the matching degree. The radiotherapy apparatus control apparatus 2 generates the matching result displays 71, 76 and 81 on the basis of the locations of the regions and the matching degrees which are calculated as mentioned above, and displays the matching result display images 71, 76 and 81 on the display unit (Step S4).

The user refers to the matching result displays 71, 76 and 81 to select a proper image for the first template from the plurality of first location measurement transmission images and then inputs data into the radiotherapy apparatus control apparatus 2 to identify the selected first location measurement transmission image (Step S12, Selection). At this time, the radiotherapy apparatus control apparatus 2 displays on the display unit, the display image 91 generated on the basis of the selected first location measurement transmission image and one second location measurement transmission image imaged simultaneously with the selected first location measurement transmission image. The radiotherapy apparatus control apparatus 2 generates the first template from the selected first location measurement transmission image on the basis of data inputted from the input unit, and generates the second template from the selected second location measurement transmission image (Step S13). The radiotherapy apparatus control apparatus 2 adds a newly-generated first template and second template and calculates the locations of regions, which are the most similar to the templates from the plurality of first location measurement transmission images and plurality of second location measurement transmission images, and the matching degree. The radiotherapy apparatus control apparatus 2 generates the matching result display images 71, 76 and 81 on the basis of the locations of the regions and the matching degrees that are calculated as mentioned above, and displays the matching result displays 71, 76 and 81 on the display unit (Step S14). Such an operation of the step S12 to step S14 are repeatedly performed, until the user inputs data into the radiotherapy apparatus control apparatus 2 to indicate that the template is not generated any more (Step S12, No-selection).

The radiotherapy apparatus control apparatus 2 restarts the operation of performing the radiotherapy, after the operation of modifying the template as mentioned above.

There is a case that through the radiotherapy, the affected site of the patient 43 is deformed, or a hiding rate of the affected site behind a bone is changed, or a motion different from a motion prior to the therapy is carried out. There is a case that such phenomena cause the decrease in the matching degree in the template matching. According to such operations, the template can be added according to the phenomenon, thereby reducing a possibility that the location of the affected site cannot be specified. Moreover, according to such operations, the user can easily recognize a type of the template to be required, and can generate it easier and faster on the basis of the first templates and the second templates. As a result, the time of the radiotherapy can be made shorter, which can reduce the burden on the patient 43.

Figure 12:
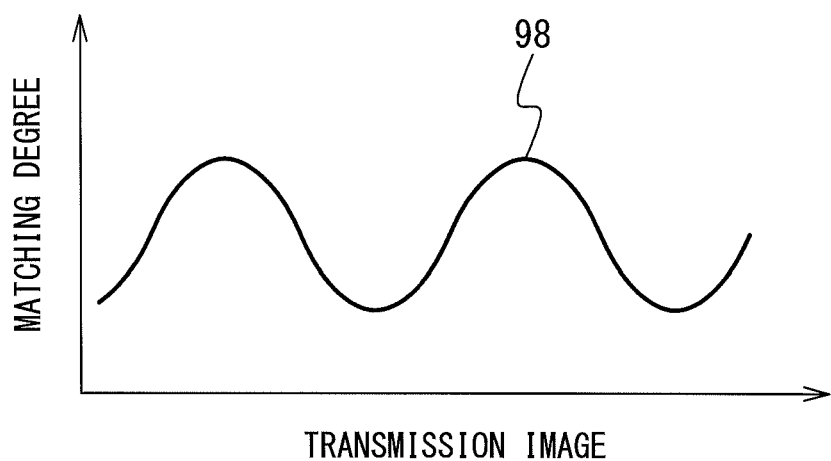
FIG. 12 is a diagram showing a display image when the templates are modified.

The radiotherapy apparatus control apparatus 2 can display other data different from data indicating whether the location of the affected site has been specified during the therapy. FIG. 12 shows an example of a display image displayed on the display unit while the operation of performing the radiotherapy is performed. The display image represents a graph of a change 98 in the matching degree. The change 98 indicates the matching degrees calculated from the plurality of transmission images that are respectively picked up at times different from each other and indicates a manner of the change in the matching degree with the elapse of the time during the therapy. According to the display image, the user can estimate whether or not a new template is required to be added, easier and more proper, which is preferable. Moreover, the user can properly determine the timing when the radiotherapy is stopped, by referring to the display image.

It should be noted that the selecting section 54 may be replaced with a different selecting section which can select a template transmission image from the plurality of transmission images without using any data inputted from the input unit. For example, the selecting section selects a first transmission image having the lowest matching degree calculated by the matching degree calculating section 52, from the plurality of first transmission images picked up by the imaging section 51. Like the radiotherapy apparatus control apparatus 2 in the above-mentioned embodiments, the radiotherapy apparatus control apparatus, which includes the selecting section, can generate a proper template and measure the affected site of the patient with higher precision. As a result, the radiotherapy can be performed on the patient with higher precision.

It should be noted that the template generating section 55 can be replaced with a different template generating section which generates a template from the transmission image without using any data inputted from the input unit. The template generating section extracts the image region of the affected site of the patient by image-processing the transmission image. Like the radiotherapy apparatus control apparatus 2 in the above-mentioned embodiments, the radiotherapy apparatus control apparatus, which includes the template generating section, can generate a proper template and can measure the affected site of the patient with higher precision. As a result, the radiotherapy can be performed on the patient with higher precision.

It should be noted that the imager system can be replaced with a different modality. As the modality, CT and MRI are exemplified. Like the radiotherapy system 1 in the above-mentioned embodiments, the radiotherapy system to which the modality is applied can generate a proper template and can measure the affected site of the patient with higher precision. As a result, the radiotherapy can be performed on the patient with higher precision.

The invention claimed is:

1. A radiotherapy system, comprising:
   a radiotherapy apparatus; and
   a radiotherapy apparatus control apparatus,
   wherein the radiotherapy apparatus comprises:
   a radiation irradiation unit that irradiates a therapeutic radiation; and
   a driving unit that changes positions of the radiation irradiation unit,
   wherein the radio therapy apparatus control apparatus comprises:
   a selecting section configured to select a plurality of template transmission images from a plurality of transmission images imaged by using radiation transmitting through a specimen;
   a template generating section configured to generate a template set including a plurality of templates based on the selected template transmission images;
   a matching degree calculating section configured to calculate a plurality of matching degrees based on each template of the template set and the plurality of transmission images;
   a display section;
   an imaging section configured to image a location measurement transmission image from the radiation transmitting through said specimen;
   a template matching section configured to perform pattern-matching of each template of said template set with said location measurement transmission image and select an optimal template which is the most similar to a portion of the location measurement transmission image, from said template set;

a location calculating section configured to calculate a location of a specific site of said specimen based on said location measurement transmission image and said optimal template;

a control unit configured to control the driving unit to drive the radiation irradiating unit to a position where the radiation irradiation unit irradiates the therapeutic radiation through said specific site location;

and an irradiating section configured to control said radiation irradiating unit to irradiate the therapeutic radiation through the specific site location, wherein said display section displays a display image on a display unit including the plurality of transmission images which are classified on the display unit based on the plurality of matching degrees, wherein said selecting section selects, in response to an instruction by a user, a template transmission image from the plurality of transmission images which are classified on the display unit based on the plurality of matching degrees, wherein the template generating section adds a new template based on the selected template transmission image and modifies the template set, wherein each of the plurality of matching degrees indicates a similarity between a portion of a corresponding one of said plurality of transmission images and one template of said template set, and wherein said display image includes a first region and a second region, wherein first transmission images of said plurality of transmission images from which the matching degrees higher than a predetermined threshold have been calculated are displayed in the first region, and wherein second transmission images of said plurality of transmission images from which the matching degrees lower than the predetermined threshold have been calculated are displayed in the second region.

2. The radiotherapy system according to claim 1, wherein said display image indicates an order of imaging of said plurality of transmission images.

3. The radiotherapy system according to claim 1, wherein said display image indicates a location of a region, which is calculated through the template-matching using said template set, of each of said plurality of transmission images.

4. The radiotherapy system according to claim 1, wherein said display image identifies said first transmission images, which have been already used to generate the template of said template set, of said plurality of transmission images, and the second transmission images, which have not been used to generate the template, of said plurality of transmission images.

5. The radiotherapy system according to claim 1, wherein said new template indicates a template region image extracted from said selected template transmission image, based on input data.

6. The radiotherapy system according to claim 5, wherein the selected plurality of transmission images is a plurality of first template transmission images, wherein the selecting section is configured to also select a plurality of second template transmission images from the plurality of transmission images, wherein one of the first template transmission images is imaged by use of radiation irradiated at a first location, wherein one of the second template transmission images is imaged by use of radiation irradiated at a second location different from the first location at a same time as when said one of the first template transmission images is imaged, wherein said new template comprises a first template for an image portion of a first template region extracted from said one of the first template transmission images, and a second template for an image portion of a second template region extracted from said one of the second template transmission images, and wherein the second template region is extracted such that a location of the second template region in a predetermined direction corresponds to a location of the first template region in the predetermined direction.

7. The radiotherapy system according to claim 1, wherein the new template is selected from second transmission images of said plurality of transmission images from which the matching degrees lower than the predetermined threshold have been calculated.

8. The radiotherapy system according to claim 1, wherein said selecting section selects the template transmission image from the plurality of transmission images which are classified on the display unit based on the plurality of matching degrees when an operation of performing radiotherapy is stopped by the user.

* * * * *